United States Patent [19]

Lane

[11] Patent Number: 5,075,112

[45] Date of Patent: Dec. 24, 1991

[54] METHOD OF AND DOSAGE UNIT FOR INHIBITING ANGIOGENESIS OR VASCULARIZATION IN AN ANIMAL USING SHARK CARTILAGE

[75] Inventor: Irwin W. Lane, Short Hills, N.J.

[73] Assignee: Cartilage Technologies Inc., Carrollton, Tex.

[21] Appl. No.: 478,526

[22] Filed: Feb. 12, 1990

[51] Int. Cl.$^5$ .......................... A61K 9/02; A61K 9/20; A61K 9/48

[52] U.S. Cl. .................................... 424/434; 424/436; 424/451; 424/464; 424/DIG. 15; 424/548; 514/966

[58] Field of Search .................. 424/451, 464, 95, 436, 424/DIG. 15; 514/966

[56] References Cited

U.S. PATENT DOCUMENTS 3,966,908  6/1976  Balassa .............................. 424/548
4,444,752  4/1984  Prudden ............................ 424/548
4,656,137  4/1987  Balassa .............................. 424/548

OTHER PUBLICATIONS

Oikawa, T., *A Novel Angiogenic Inhibitor Derived from Japanese Shark Cartilage (I)*, Cancer Letters, vol. 51, pp. 181-186, 1990.

Lee, A., *Shark Cartilage Contains Inhibitors of Tumor Angiogenesis*, Science, vol. 221, pp. 1185-1187, 1983.

Leur, C. A., *Inhibitors of Angiogenesis from Shark Cartilage*, Tumor Biology, abstract 4624, p. 949.

D'Amore, P., *Antiangiogenesis as a Strategy for Antimetastasis*, Seminars in Thrombosis & Hemostasis, vol. 14, No. 1, 1988.

Folkman, J., *Vascularization of Tumors*, Sci. Am. 234:58-73, 1976.

Folkman, J. and Klagsburn, M., *Angiogenic Factors*, Science, vol. 235, pp. 442-447, Jan. 1987.

Primary Examiner—Thruman K. Page
Assistant Examiner—Amy Hulina

[57] ABSTRACT

Method of, and dosage unit for, inhibiting angiogenesis in an aminal having an intestinal wall by administering to the animal, orally or anally, an effective amount of shark cartilage, particularly finely divided shark cartilage in solid dosage form such as a tablet, capsule, suppository, for passing through the intestinal wall of the animal as a suspension.

10 Claims, 5 Drawing Sheets

*EFFECT OF CARTILAGE ADMINISTRATION AGAINST A HUMAN MELANOMA XENOGRAFT (MeXF 514) IN NUDE MICE*

|  | DAY 0 | DAY 4 | DAY 7 | DAY 11 | DAY 14 | DAY 21 |
|---|---|---|---|---|---|---|
| CARTILAGE AT 1200 mg/kg P.O. DURING 21 DAYS | INITIAL VOLUME: 41mg | Vt/Vo=0.70 | Vt/Vo=0.587 | Vt/Vo=0.423 | Vt/Vo=0.423 | Vt/Vo=0.593 |
| CONTROL | INITIAL VOLUME: 39mG | Vt/Vo=0.712 | Vt/Vo=0.693 | Vt/Vo=0.693 | Vt/Vo=0.912 | Vt/Vo=1.942 |
| TUMOR WEIGHT T/C X 100 |  | 98 | 84 | 61 | 46 | 30 |

FIG. 1

EFFECT OF CARTILAGE ADMINISTRATION AGAINST A HUMAN MELANOMA XENOGRAFT (MeXF 514) IN NUDE MICE

| | DAY 0 | DAY 4 | DAY 7 | DAY 11 | DAY 14 | DAY 21 |
|---|---|---|---|---|---|---|
| CARTILAGE AT 1200 mg/kg P.O. DURING 21 DAYS | INITIAL VOLUME: 41mg | $V_t/V_o=0.70$ | $V_t/V_o=0.587$ | $V_t/V_o=0.423$ | $V_t/V_o=0.423$ | $V_t/V_o=0.593$ |
| CONTROL | INITIAL VOLUME: 39mG | $V_t/V_o=0.712$ | $V_t/V_o=0.693$ | $V_t/V_o=0.693$ | $V_t/V_o=0.912$ | $V_t/V_o=1.942$ |
| TUMOR WEIGHT T/C X 100 | | 98 | 84 | 61 | 46 | 30 |

CORRELATION OF SIZE OF AFFECTED ZONE WITH VASCULAR INDEX FOR LOT 1 OF SHARK CARTILAGE OF THE PRESENT INVENTION COMPARED TO HYDROCORTISONE/HEPARIN (HC+HEP) AND BLANK AGAROSE

CORRELATION OF SIZE OF AFFECTED ZONE WITH VASCULAR INDEX FOR LOT 2 OF SHARK CARTILAGE OF THE PRESENT INVENTION COMPARED TO HYDROCORTISONE/HEPARIN (HC+HEP) AND BLANK AGAROSE

CORRELATION OF SIZE OF AFFECTED ZONE WITH VASCULAR INDEX FOR LOT 3 OF SHARK CARTILAGE OF THE PRESENT INVENTION COMPARED TO HYDROCORTISONE/HEPARIN (HC+HEP) AND BLANK AGAROSE

CORRELATION OF SIZE OF AFFECTED ZONE WITH VASCULAR INDEX FOR LOT 4 OF SHARK CARTILAGE OF THE PRESENT INVENTION COMPARED TO HYDROCORTISONE/HEPARIN AND BLANK AGAROSE

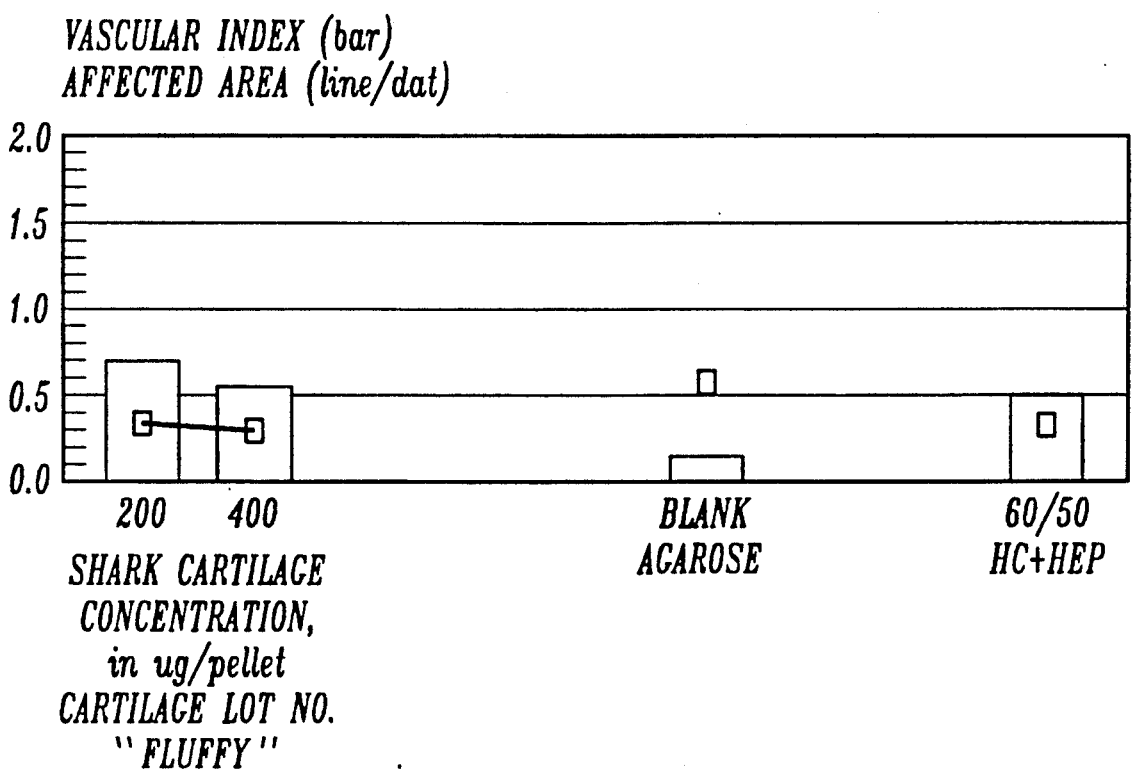

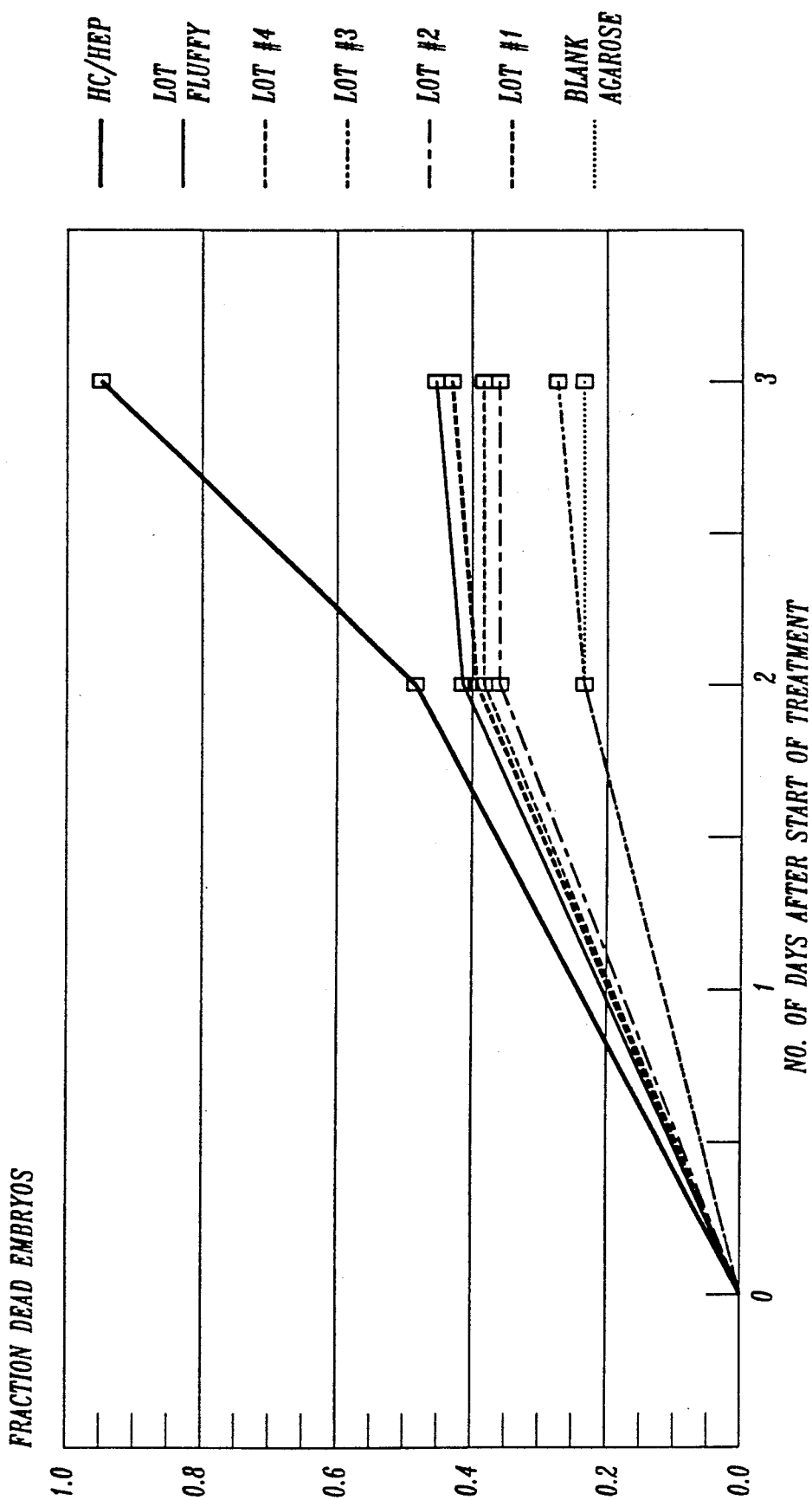

METHOD OF AND DOSAGE UNIT FOR INHIBITING ANGIOGENESIS OR VASCULARIZATION IN AN ANIMAL USING SHARK CARTILAGE

BACKGROUND OF THE INVENTION

This invention relates generally to a method of, and a dosage unit for, inhibiting angiogenesis or vascularization in an animal, and more particularly relates to a a method of, and a dosage unit for, inhibiting angiogenesis or vascularization in an animal having an intestinal wall utilizing an effective amount of shark cartilage, particularly finely divided shark cartilage, for passing through the intestinal wall as a suspension for inhibiting, inter alia, tumor growth and metastasis, in particular Kaposi sarcoma; arthritis, in particular rheumatoid arthritis; diabetic retinopathy and neovascular glaucoma; psoriasis and inflammatory diseases with vascular component.

It is known, or has been at least substantially established, that blood vessel growth, development or formation, referred to variously in the art as angiogenesis and vascularization, and referred to hereinafter as angiogenesis, is associated with disease such as diabetic retinopathy, neovascular glaucoma, rheumatoid arthritis and tumor growth and metastasis; Folkman, J., *Vascularization of Tumors*, Sci. Am. 234:58–73, 1976; Lee, A. and Langer, R., *Shark Cartilage Contains Inhibitors of Tumor Angiogenesis*, Science, Vol. 221, pp. 1185–1187, 1983; Folkman, J. and Klagsburn, M., *Angiogenic Factors*, Science, Vol. 235, pp. 442–447, January 1987; and D'Amore, P., *Antiangiogenesis as a Strategy for Antimetastasis*, Seminars in Thrombosis and Hemostasis, Vol. 14, No. 1, 1988, ©1988 by Thieme Medical Publishers, Inc., 381 Park Avenue South, New York, New York 10016.

SUMMARY OF THE INVENTION

It has been found, and in summarizing generally the following more particular teachings of the present invention, that angiogenesis may be inhibited in an animal having an intestinal wall by administering to the animal, orally or anally, an effective amount of shark cartilage, particularly finely divided shark cartilage powder in solid dosage form such as tablet, capsule or suppository, for passing through the intestinal wall as a suspension.

DESCRIPTION OF THE DRAWINGS

FIG. 1 is a Table illustrating the effect of shark cartilage administration against a human melanoma xenograft (MeXF 514) in nude mice;

FIGS. 2–6 are graphs showing correlation of size of affected zone of a CAM with vascular index for the given lot of shark cartilage applied to the CAM compared to hydrocortisone/heparin and blank agarose applied to the CAM; and FIG. 7 is a graph illustrating chicken embryo mortality in the CAM assays as a function of treatment over three days with different lots of shark cartilage, hydrocortisone/heparin and blank agarose.

DESCRIPTION OF THE PREFERRED EMBODIMENT

Figure 2:
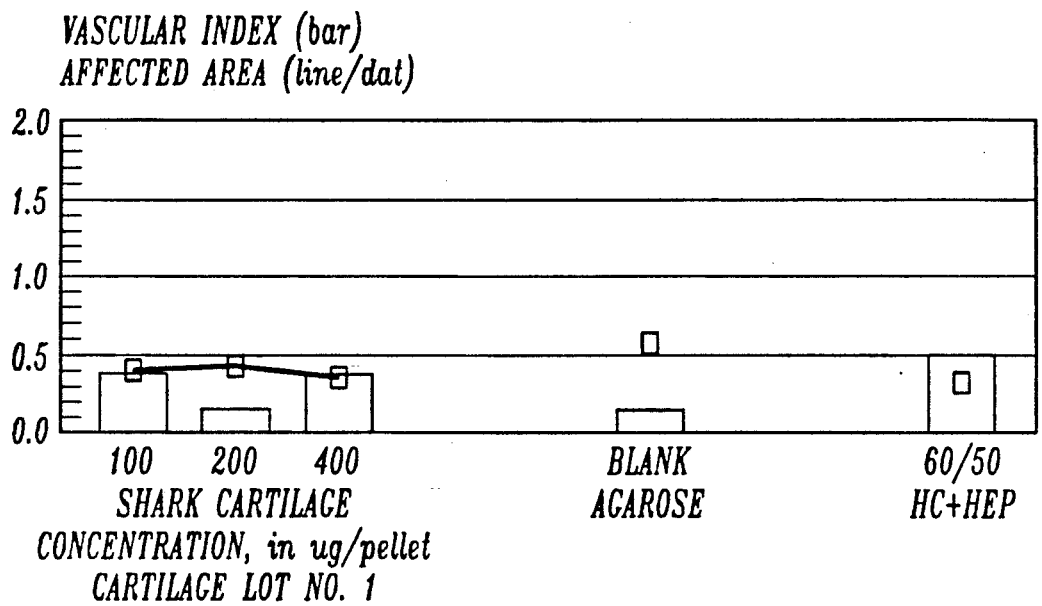

In accordance with the further teachings of the present invention, it has been found that an effective dose, or dosage unit, of shark cartilage, particularly finely divided shark cartilage powder, for inhibiting angiogenesis is about 1 gram to about 2 grams per day per each 15 pounds of body weight of the animal, particularly 1 gram per day per each 15 pounds of body weight of the animal; smaller amounts, e.g. about 0.2 gram to about 0.5 gram per day per each 15 pounds of body weight of the animal are effective amounts for maintaining the inhibiting of, or for preventing, angiogenesis.

FIG. 1 is a Table illustrating the effect of shark cartilage of the present invention administration against a human melanoma xenograft in nude mice which effect, in accordance with the teachings of the present invention, was due to the inhibition of angiogenesis. The Table of FIG. 1 compares the average effect during 21 days of the administration of shark cartilage at a dosage unit of 1,200 mg/kg of body weight against the volume and weight of human melanoma xenograft implanted in a tested group of 10 nude mice versus the average volume and weight of human melanoma xenograft implanted in a control group of 10 nude mice to which no shark cartilage was administered during the 21 days. Particularly it will be noted that the nude mice in the test group to which the shark cartilage was administered experienced, by the 21st day, an average tumor volume of approximately 59% of the average volume of the original tumors whereas the nude mice in the control group to which no shark cartilage was administered experienced, by the 21st day, an average tumor volume of 194% of the average volume of the original tumors, From the last line of the Table of FIG. 1, it will also be noted that the average tumor weight of the tumors in the control group of nude mice to which no shark cartilage was administered was 3.33 times heavier than the average tumor weight in the test group of nude mice to which shark cartilage was administered.

It is believed that the above Table illustrates, and in accordance with the teaching of the present invention, that the shark cartilage administered against human melanoma xenograft in the nude mice of the test group inhibited angiogenesis thereby resulting in a reduction in tumor volume and a reduction in tumor weight over the test period.

It will be understood that the shark cartilage useful in the method of the present invention may be prepared by any suitable means or process to result in shark cartilage which is substantially pure shark cartilage, substantially free from adhering tissue. Preferably, shark cartilage particularly useful in the practice of the method of the present invention is prepared by cleaning the shark cartilage physically or through hydrolysis to remove adhering tissue; with regard to the bones of the shark, the internal blood vessels and nervous systems present in the back bone or spinal column are augered out, resulting in substantially 100% pure shark cartilage. The shark cartilage is then dried in a convection oven to approximately 15% moisture and is then dried in a vacuum to approximately 1% moisture with the vacuum drying temperature not being allowed to substantially exceed 100° F. Thereafter, the shark cartilage is pulverized under inert gas (typically nitrogen) conditions under refrigerated conditions with the temperature not being allowed to exceed substantially 100° F. Thereafter, the shark cartilage is screened to substantially 300 mesh producing finely divided shark cartilage for passage through the intestinal wall of an animal, approximately 82% of which cartilage is about 45 microns in size or less, after which the finely divided shark cartilage is sterilized and then provided in solid dosage form such as capsule form, suppository form, tablet form.

Figure 4:
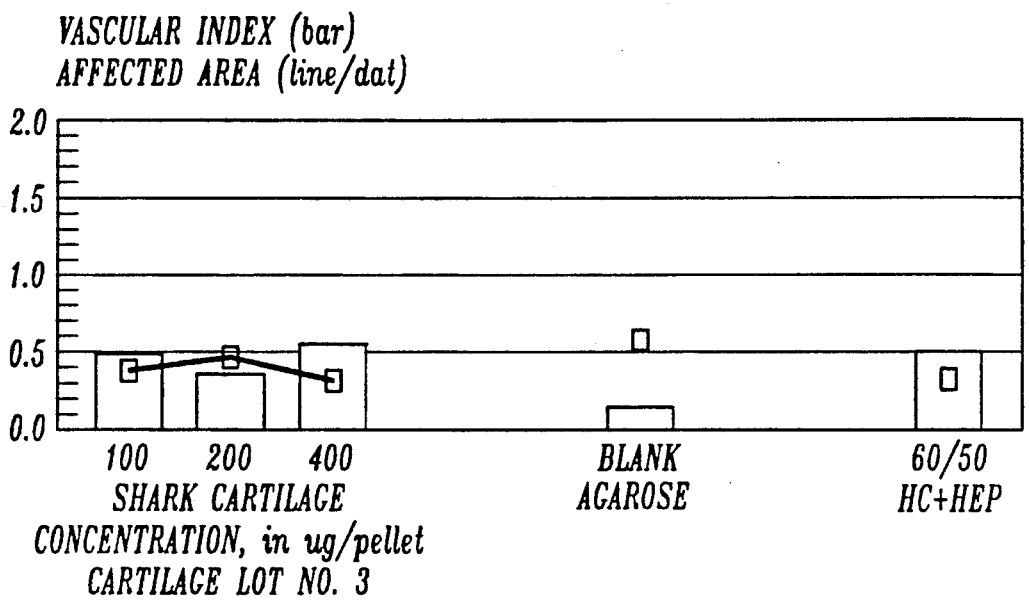
Figure 5:
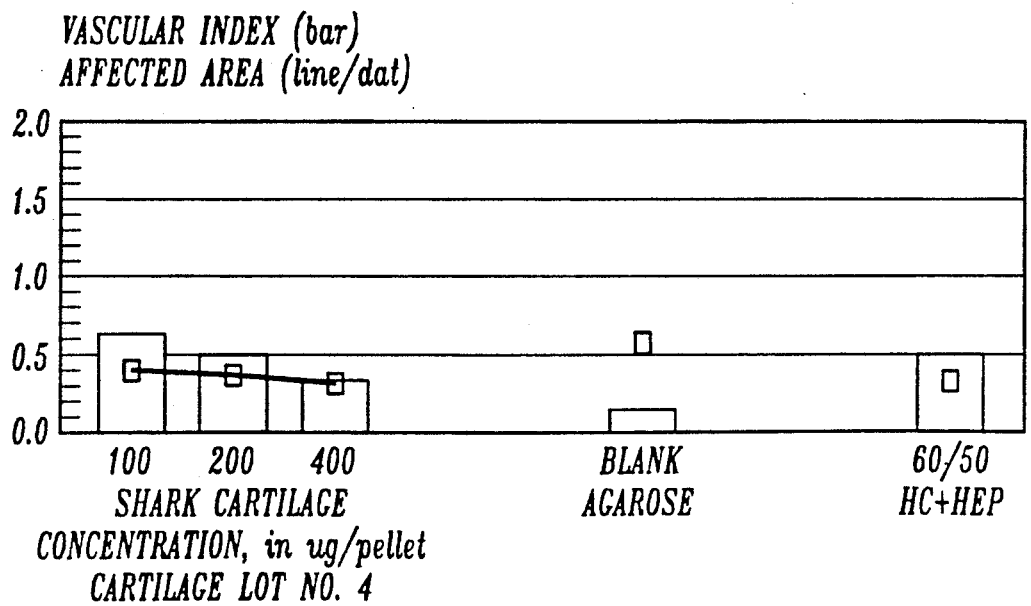

Referring now to FIGS. 4–7, further utility of the teachings of the present invention in inhibiting angiogenesis or vascularization in an animal using shark cartilage will be demonstrated. As known to those skilled in the art, the chicken chorioallantoic membrane (CAM) assay is a known method or procedure for demonstrating the effectiveness of an antiangiogenic substance or a substance for inhibiting angiogenesis or vascularization in an animal. In the CAM assay, as is known, a fertile chicken egg is prepared for testing by either of two procedures referred to in the art as the window or egg culture techniques. In both techniques, the fertilized chicken eggs are maintained, typically in a humidified incubator, at a certain temperture, e.g. 36°-37° C., and in a horizontal position with twice daily rotations. In the case of the window technique, an air pocket is created in the egg, often by withdrawing albumen, and by a particular day after fertilization, e.g. the eighth day, a window e.g. a 1.5-2.5cm$^2$ window, was cut from the shell directly over the air pocket. The underlying shell membrane is carefully removed exposing a CAM that is undamaged and free from any shell or shell membrane fragments. In the egg culture technique, typically sterile techniques are employed in transferring the fertilized egg at a particular day, e.g. 3–4 to a petri dish containing a tissue culture medium and, in some instances, anti-fungal/anti-bacterial agents. Until the start-up of the test, the egg cultures are incubated at a particular temperature, e.g. 36-37° C. in a humidified atmosphere, typically containing 1-2% $CO_2$. The advantages as known to the art of the culture method over the window method are the ready access to the cam surface, including access for microscopic observation and the availability of a larger surface for testing. As stated, these techniques are well known to those skilled in the art.

Figure 3:
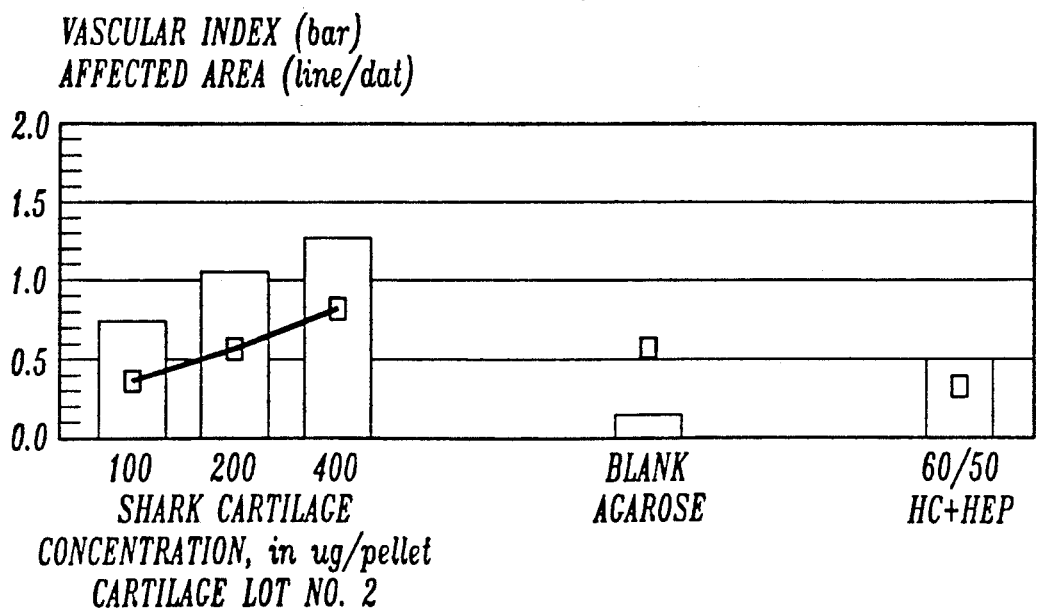

In obtaining the data from which the graphs of FIGS. 2-7 are produced, CAM assays for determining the angiogenic properties of the shark cartilage of the present invention on the CAM were performed using the egg culture technique. Fertilized White Leghorn Eggs were used, were removed from the shell on the third day after fertilization and placed in a culture dish. The cultured eggs were maintained through day 6 at 37° C. in an atmosphere of 2% $CO_2$ and a relative humidity of 70%. After day 6, incubation was carried out without supplemental $CO_2$. The eggs used for this CAM study were received on the third day after fertilization and were cracked directly. Four hundred eight (408) eggs were cracked yielding 339 eggs to be put on test 3 days later and 243 eggs were read at the end of the test, 5 days after cracking. As may be noted from the legend at the top of FIGS. 2–6, 5 different lots of shark cartilage of the present invention were utilized in the CAM assays and, as will be noted from the lower lefthand portion of FIGS. 2–6, 3 different concentrations of the shark cartilage of the present invention were used, namely 100, 200, and 400μg/pellet were used—the shark cartilage of the present invention was formed into pellets in these concentrations, using low gelling temperature agarose, and the pellets implanted on the CAMs. As may be further noted from the lower lefthand portion of FIG. 6, "FLUFFY," sonification was used on the shark cartilage of the present invention and the low gelling temperature agarose to determine the effect, if any, of sonification or "FLUFFY" on the dispersion of the pellet into the CAM. The pellets were placed on day 6 in the CAMs using only one pellet per egg or per CAM and dispersed into the CAMs. For each of the 6 lots, FIGS. 2-6, 6, 21-22 pellets as noted above were implanted, one per egg, and information was obtained at the end of the run of each lot on an average of about 15 CAMs per lot.

Two days after implantation and incubation at 37° C., the CAMs were evaluated to determine the antiogenic effects of the shark cartilage of the present invention on the CAMs. The evaluation was performed by two independent readers. The identities of the contents of the above-noted pellets were not revealed to the readers until after the completion of the readings on the second day of testing. The area around the pellets on the CAMs and up to 2 microscopic fields away (or up to 3–4 pellet diameters away) was examined under a microscope. The vascularity around, but not under, the pellets was evaluated using test grades of 0, 1, or 2 as follows:

1) A score of 0 indicated that NO CHANGE in blood vessel number was apparent in the comparisons with other areas slightly removed from the pellet.
2) A score of 1 indicated REDUCED VASCULARITY around the pellet.
3) A score of 2 indicated the ABSENCE of capillaries and other small blood vessels in the area around the pellet.

In addition, inhibition of chicken egg embryonic angiogenesis was further described in quantitative terms by measuring the size of the affected zone surrounding the pellet as well as the portion of the pellet that borders the affected region.

| | |
|---|---|
| Pellet Circ. Ave. = | Average fraction of pellet circumference bordering the vascular effect. |
| Microscopic Fld. Ave. = | Average number of microscopic fields altered by the vascular effect. A microscopic field is approximately 35 nm$^2$. |

The data obtained by the methods outlined above were processed according to the following procedures and recorded in a dBASE III file.

| | |
|---|---|
| Total Number at Start | CAMs with Reduced Vascularity |
| Total Number Dead at End | Total Number |
| Total Number Alive at End | Average Pellet Circumference |
| Total Number with Pellet off of CAM | that borders affected area |
| | Average Size of affected area |
| | CAMs with Avascular Zones |
| | Total Number |
| | Average Pellet Circumference |
| | that borders affected area |
| | Average Size of affected area |

The data for each reader from each lot were treated separately. Appropriate averages were next determined from the results of both readers. The final averages were then obtained from the averages of the two runs.

The Total Number of Chicken Eggs, or CAMs, Read equaled the Total at the Start less the Total Dead (after completion of the 2 day test) less the Total Number of Eggs in which the pellet was no longer on the CAM. The Total Eggs Alive at the End equaled the sum of the Total Read and Total with Free Pellets (or the Total at the Start less the Total Dead).

The Total Number of Eggs with areas of Reduced Vascularity or with Avascular Zones was determined for each reader. The average fraction of the pellet circumference bordering the affected area and the average size of the affected CA surface (in microscopic fields) were determined using data from each reader. In addition, the value for all affected areas (those with reduced vascularity or avascularity) was determined by combining the data for zones with reduced vascularity and avascular zones.

The values for the Vascular Index were calculated from each reader's data using the following formula:

VASCULAR INDEX [V.I.]

$$V.I. = \frac{a \times 0 + b \times 1 + c \times 2}{a + b + c} \text{ [MAX. VALUE = 2.0]}$$

where
- a = Number of CAM with 0 Rating [=Normal Degree of Vascularization]
- b = Number of CAM with 1 Rating [=Apparent Decrease in Capillary Number in Zone]
- c = Number of CAM with 2 Rating [=No Apparent Capillaries in Zone ("Avascular Zone")]
- a+b+c = Total Alive - Total Pellet Free [Total Number of Usable Embryos at End of Test]

The results from the 2 readers for a given lot were processed to give average values for the size of the effects and the index values; these values are shown at the lower lefthand portion of FIGS. 2-6.

In the manner further known to those skilled in the art, to determine the antiangiogenic effect of a substance, the antiangiogenic effect of such substances is compared against the known effect of known antiangiogenic substances referred to typically in the art as a control. Two controls were used to determine the comparative antiangiogenic effects, inhibition of angiogenesis or vascularization, of the shark cartilage in accordance with the teachings of the present invention. These two controls were blank agarose and hydrocortisone (HC, 60µg/pellet) with heparin (Hepar Industries, 50 µg/pellet) referred to hereinafter and in FIGS. 2-6 as 60/50 HC+HEP. As known to those skilled in the art, 60/50 HC+HEP is a known standard or control against which antiangiogenic substances are compared to determine their antiangiogenic effect.

With regard to the comparison of the shark cartilage pellets of the present invention on the CAMs with blank agarose, blank agarose pellets were placed on 14 CAMs and examined using the procedure noted above, and it was determined that only 2 of the 14 CAMs displayed even a modest degree of reduced vascularity around the agarose pellets, note the graph for blank agarose at the middle lower portion of FIGS. 2-6.

With regard to the 60/50 HC+HEP control, 21 pellets of 60/50 HC+HEP pellets were placed on 21 CAMs and the same testing procedure noted above for the shark cartilage pellets of the present invention was used, and it was determined that the average Vascular Index, as determined above, was 0.50 which Vascular Index number may be noted at the lower righthand portion of FIGS. 2-6.

Referring again to FIGS. 2-6, the comparative antiangiogenic effect of the shark cartilage of the present invention compared to the antiangiogenic effect of the controlled blank agarose and 60/50 HC+HEP will be noted. From FIGS. 2, 4 and 5, it will be noted that the shark cartilage of the present invention displayed substantially the same antiangiogenic effect as the 60/50 HC+HEP whereas the "FLUFFY" illustrated in FIG. 5 displayed slightly greater antiangiogenic effect than the control 60/50 HC+HEP. Significantly, and referring to FIG. 3, the shark cartilage of the present invention of lot 2 displayed significantly greater antiangiogenic effect than the 60/50 HC+HEP control particularly the larger 200 and 400µg shark cartilage pellets. Consequently, and in accordance with the teachings of the present invention, the shark cartilage of the present invention inhibits angiogenesis or vascularization in an animal or produces an antiangiogenic effect.

Lastly, and referring to FIG. 7, the embryo mortality of the chicken eggs, embryo within the CAM, was determined as a function of treatment over 3 days with the 5 different lots of shark cartilage of the present invention (FIGS. 2-7) and compared against the controls blank agarose and 50/60 HC+HEP. From FIG. 7, it will be noted, particularly from the solid line reaching the highest ordinate index and indicating the embryo mortality of the control 60/50 HC+HEP, that the shark cartilage of the present invention experienced, significantly, much lower embryo mortality, and an indication that the shark cartilage of the present invention has much less toxicity than 50/60 HC+HEP, an indication of safety for animal usage for inhibiting angiogenesis or vascularization in accordance with the teachings of the present invention.

It will be understood by those skilled in the art that many modifications and variations may be made in the present invention without departing from the spirit and the scope thereof.

What is claimed is:

1. A method of inhibiting angiogenesis in an animal having an intestinal wall comprising administering to said animal an effective amount of shark cartilage for passing through said intestinal wall as a suspension, said effective amount being about 0.2 gram to about 2 grams per day per each 15 lbs. of body weight of said animal, said shark cartilage being administered in solid dosage form selected from the group consisting of a capsule, a table and a suppository and said solid dosage form prepared from shark cartilage screened to substantially 300 mesh.

2. Method according to claim 1 wherein said effective amount is about 0.2 gram to about 2 grams per day per each 15 lbs. of body weight of said animal.

3. Method according to claim 2 wherein said effective amount is about 1 gram to about 2 grams per day per each 15 lbs. of body weight of said animal.

4. Method according to claim 2 wherein said effective amount is about 1 gram per day for each 15 lbs. of body weight of said animal.

5. Method according to claim 2 wherein said method is particularly useful for maintaining said inhibiting of angiogenesis and wherein said effective amount is about 0.2 gram to about 0.5 gram per day per each 15 lbs. of body weight of said animal.

6. Method according to claim 1 wherein said shark cartilage is finely divided shark cartilage.

7. Method according to claim 6 which comprises administering said shark cartilage in a solid dosage form.

8. Method according to claim 7 wherein said solid dosage is a capsule.

9. Method according to claim 7 wherein said solid dosage form is a tablet.

10. Method according to claim 7 wherein said solid dosage form is a suppository.

* * * * *